(12) United States Patent
Alesi et al.

(10) Patent No.: US 7,670,318 B2
(45) Date of Patent: Mar. 2, 2010

(54) NEEDLE SAFETY DEVICE WITH TORTUOUS PATH

(75) Inventors: Daniel E. Alesi, Keene, NH (US); David R. MacLean, Chesterfield, NH (US)

(73) Assignee: Smiths Medical ASD, Inc., Keene, NH (US)

( * ) Notice: Subject to any disclaimer, the term of this patent is extended or adjusted under 35 U.S.C. 154(b) by 1284 days.

(21) Appl. No.: 09/920,860

(22) Filed: Aug. 3, 2001

(65) Prior Publication Data
US 2003/0028152 A1 Feb. 6, 2003

(51) Int. Cl.
*A61M 5/00* (2006.01)
(52) U.S. Cl. .................. 604/181; 604/110; 604/192
(58) Field of Classification Search ............ 604/192, 604/195, 198, 181, 240–3, 263, 110
See application file for complete search history.

(56) References Cited

U.S. PATENT DOCUMENTS

| 4,402,682 | A | * | 9/1983 | Garver et al. | 604/111 |
| 5,030,209 | A | | 7/1991 | Wanderer et al. | |
| 5,139,489 | A | * | 8/1992 | Hollister | 604/192 |
| 5,154,285 | A | * | 10/1992 | Hollister | 604/192 |
| 5,277,311 | A | * | 1/1994 | Hollister | 604/192 |
| 5,490,841 | A | * | 2/1996 | Landis | 604/110 |
| 5,624,402 | A | * | 4/1997 | Imbert | 604/111 |
| 5,647,849 | A | * | 7/1997 | Kalin | 604/111 |
| 5,823,997 | A | * | 10/1998 | Thorne | 604/110 |
| 5,928,200 | A | | 7/1999 | Thorne et al. | |
| 6,027,482 | A | * | 2/2000 | Imbert | 604/256 |
| 6,224,576 | B1 | * | 5/2001 | Thorne et al. | 604/198 |
| 6,298,541 | B1 | * | 10/2001 | Newby et al. | 29/458 |

FOREIGN PATENT DOCUMENTS

WO 98/19723 5/1998

* cited by examiner

*Primary Examiner*—Kevin C Sirmons
*Assistant Examiner*—Phillip Gray
(74) *Attorney, Agent, or Firm*—Louis Woo

(57) ABSTRACT

A prepackaged safety needle device has fitted to a holder a double-ended needle assembly and a needle protection housing pivotally connected to the neck of the housing. The hub of the double-ended needle is mated to the neck of the holder. A circumferential sleeve extending from the neck of the holder envelops the hub so that when the needle that extends away from the holder is capped by a sheath, the lower portions of the sheath would coact with the sleeve to form a relatively tight fit. The configurations of the sleeve and the sheath with respect to the needle hub, at their respective interacting portions are such that a tortuous path is established which allows sterilizing gas to pass into the space capped by the sheath, but yet prevents bacteria or other contaminants from intruding into the space. The opening at the end of the holder away from the needle assembly is sealed by a porous cover that allows sterilizing gas to pass into the interior of the holder while acting as a barrier to prevent bacteria from entering into the holder. Thus, configured, the prepackaged device is a convenient to use device that remains sterile until use.

26 Claims, 3 Drawing Sheets

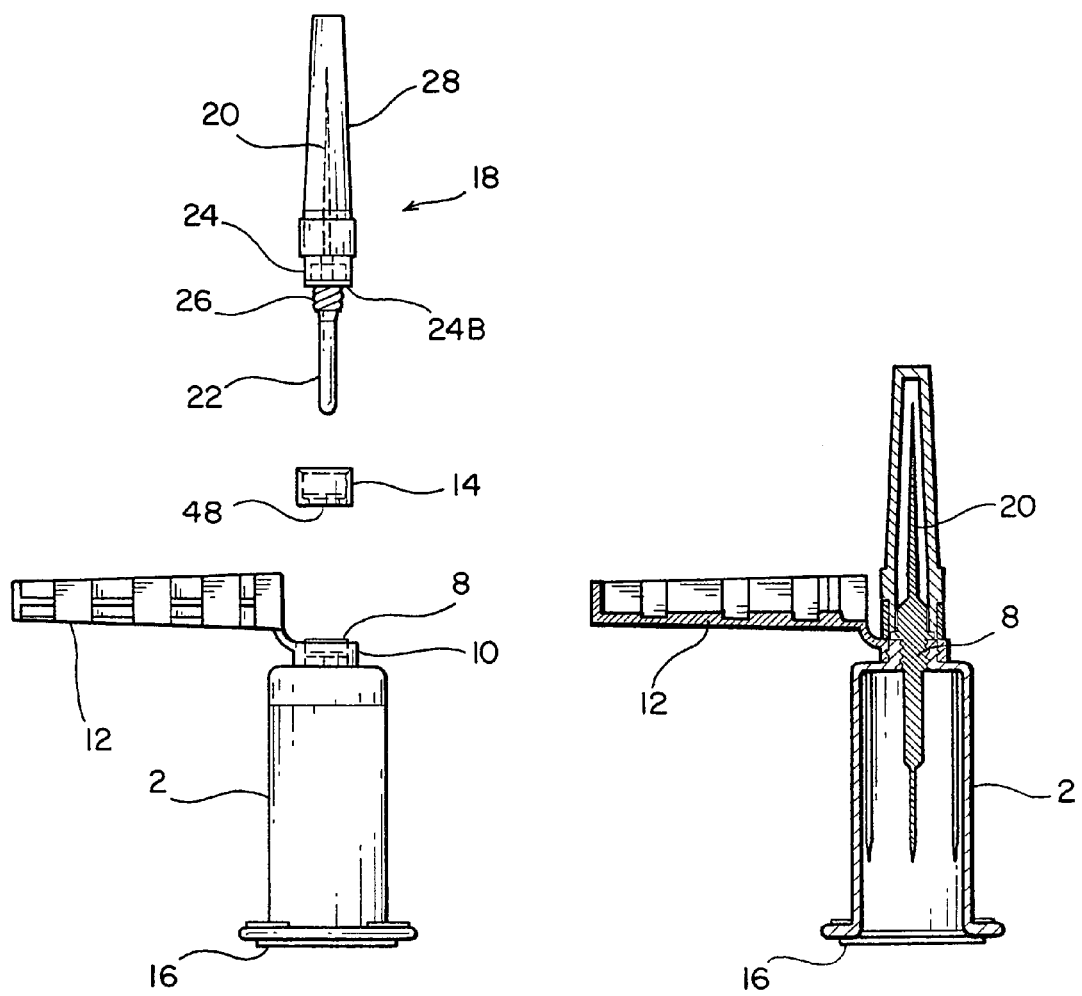

NEEDLE SAFETY DEVICE WITH TORTUOUS PATH

FIELD OF THE INVENTION

The present invention relates to needle safety devices, and more particularly a sterile blood collection device that features a needle protection housing.

BACKGROUND OF THE INVENTION

In the blood drawing devices disclosed in Hollister U.S. Pat. Nos. 5,139,489 and 5,154,285, a Vacutainer holder has fitted thereto a pivotable housing for covering a contaminated cannula of a double-ended needle that is threaded to the Vacutainer holder. The disclosures of the '489 and '285 patents are incorporated by reference herein. Although work well, the devices of the '489 and '285 patents require that the user thread a double-ended needle assembly to the Vacutainer holder before use. For the user to thread the double-ended needle assembly to the Vacutainer holder, the protective cap that keeps the double-ended needle sterile needs to be removed first. Accordingly, even before the device is used, there is the problem that the end of the double-ended needle assembly that fits into the Vacutainer holder may become non-sterile. So, too, given the fact that the Vacutainer holder is shipped without any protection, the inside of the holder is non-sterile to begin with.

Furthermore, for those Vacutainer holders that do not have the protective housing disclosed in the '489 and '285 patents, a phlebotomist tends to reuse the Vacutainer holder for drawing blood from multiple patients. To wit, once a double-ended needle assembly that has been threaded into the Vacutainer holder is contaminated, the phlebotomist will unthread the contaminated needle assembly and discard the same. A new double-ended assembly is then threaded into the same Vacutainer holder, so as to be used for the next patient. As a consequence, cross-contamination may occur at the inside of the Vacutainer holder, as blood collected from the earlier patient may have been splattered to the inside of the Vacutainer holder, so that blood collected from a later patient may be contaminated by the earlier drawn blood.

BRIEF DESCRIPTION OF THE PRESENT INVENTION

To provide a convenient to use blood drawing device that is sterile before use, the present invention device comprises a Vacutainer holder modified to include a sleeve extending from the neck of the holder. A double-ended needle assembly is fitted to the neck of the holder, by either threaded thereinto with a given torque, press fit or some other method, so that the double-ended needle assembly is already fitted to the holder for shipping. To provide sterility, a sheath is matingly fitted to the sleeve that extends from the neck of the holder. Once assembled together, the respective configurations of the sleeve, the sheath and the base of the needle assembly are such that a tortuous path is provided in the assembled device that allows gas such ethylene-oxide (ETO) to pass through to the inside of the sheath to sterilize the space inside the sheath, which includes the needle enveloped by the sheath, but acts as a barrier to prevent bacteria or other contaminant infusion to the space inside the sheath.

To ensure a sterile environment inside the Vacutainer holder, a barrier sheet that allows sterilizing gas to pass but prevents bacteria from passing seals, for example by heat seal, the open end of the Vacutainer holder wherethrough the vacuum blood collection tube is inserted. To prevent any tampering of the device, a tamper evident seal is provided at the junction where the sheath meets the sleeve. A broken tamper evident seal indicates that the device has been tampered with and that it no longer is sterile.

Similar to the aforenoted '489 and '285 patents, a needle protection housing is attached to the Vacutainer holder by means of a collar that fits about the neck of the holder. The housing is flexibly attached to the collar to be pivotable relative thereto so that, once the sheath has been removed from the sleeve and the needle used, the housing may be pivoted to a position along the longitudinal axis of the holder to cover the contaminated needle. To ensure that the needle continues to be covered by the housing, a hook mechanism integral of the housing grabs the needle as the housing is pivoted toward the needle so that, once the housing reaches the alignment position, the needle is grasped and fixedly retained by the hook mechanism. An alternative way of ensuring that the needle continues to be covered by the housing is by means of a Side Snap™ mechanism whereby at least one locking portion at the housing coacts with at least another locking portion at either the sleeve or the collar of the housing so that, once the housing is pivoted along the longitudinal axis of the device, the housing would be held along that longitudinal axis by the respective coacting locking portions. A combination of both the integral hook mechanism and the Side Snap™ locking mechanism may be used for the device of the instant invention.

The sleeve to which the sheath fits may integrally extend from the neck of the Vacutainer holder. Alternatively, the sleeve may be a separate piece shaped in the form of a cup having an opening that matches the opening of the neck of the holder. The threaded portion of the base of the double-ended needle assembly passes through the open end of the sleeve, as it is threaded to the neck of the holder. Once fully threaded, the sleeve forms a seal to the neck of the holder, and establishes the tortuous path with the sheath and the base of the needle assembly, when the open end of the sheath is fitted thereto.

It is therefore an objective of the present invention to provide a blood drawing device that a user does not have to put together.

It is another objective of the present invention to provide a blood drawing device that is sterile.

It is yet another objective of the present invention to provide a blood drawing device that could only be used one time so as to prevent potential cross contamination.

It is still yet another objective of the present invention to provide a blood drawing device that could readily be sterilized and remain sterilized until use.

BRIEF DESCRIPTION OF THE FIGURES

The above-mentioned objectives and advantages of the present invention will become more apparent and the invention itself will be best understood by reference to the following description of the present invention taken in conjunction with the accompany drawings, wherein:

FIG. 7 is a disassembled side view of a second embodiment of the instant invention; and FIG. 8 is an assembled view of the second embodiment of the instant invention.

DETAILED DESCRIPTION OF THE INVENTION

Figure 1:
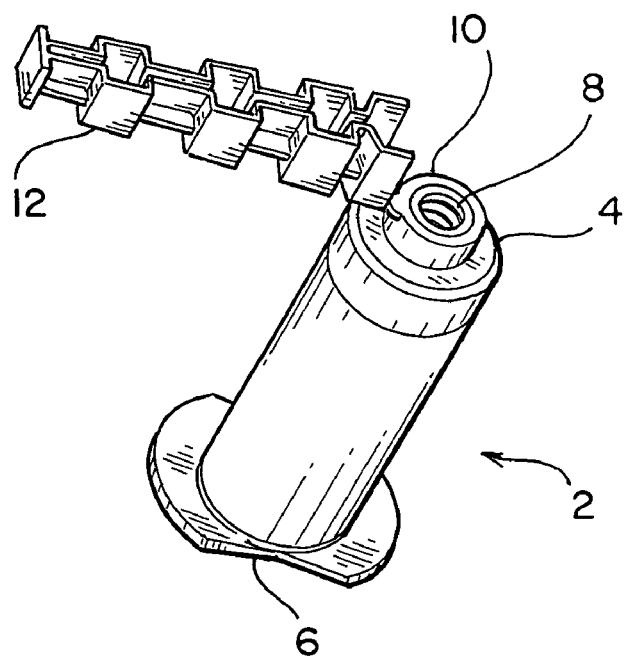
FIG. 1 is a perspective view of the safety device disclosed in the '285 patent.

As shown in FIG. 1, the device disclosed in the above incorporated by reference '285 patent has a holder 2 having a proximal end 4 and a distal end 6. A neck 8 extends from proximal end 4. Fitted about neck 8 is a collar 10 to which a housing 12 is pivotally connected by means of a living hinge. Collar 10 is rotatably fitted about neck 8 so that housing 12 is rotatable relative to neck 8. The fitting of collar 10 about neck 8 is with sufficient friction such that on once housing 12 is rotated to a given orientation with respect to neck 8, it will stay there unless or until a force is applied thereagainst.

Figure 3:
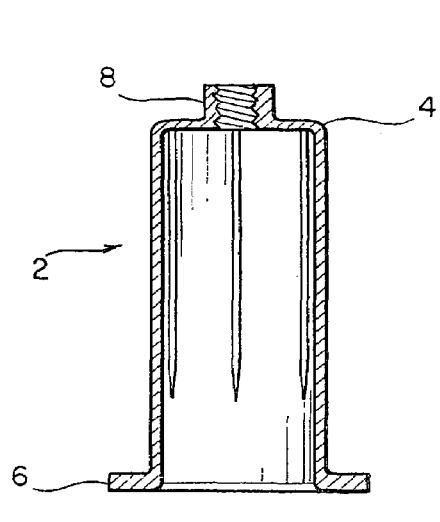
FIG. 3 is a prior art Vacutainer holder.

To use, a double-ended needle assembly is threaded into neck 8 by way of its base so that one end of the double-ended needle would extend away from holder 2 while the other end of the double-ended needle extends within holder 2. Blood withdrawn from the patient is collected by a vacuum tube inserted to holder 2 at distal end 6. See also the prior art holder shown in FIG. 3.

With reference to FIGS. 2 and 4-6, the device of the instant invention is shown. Components of the device of the instant invention which are similar to those of the FIG. 1 device are labeled the same.

Figure 4:
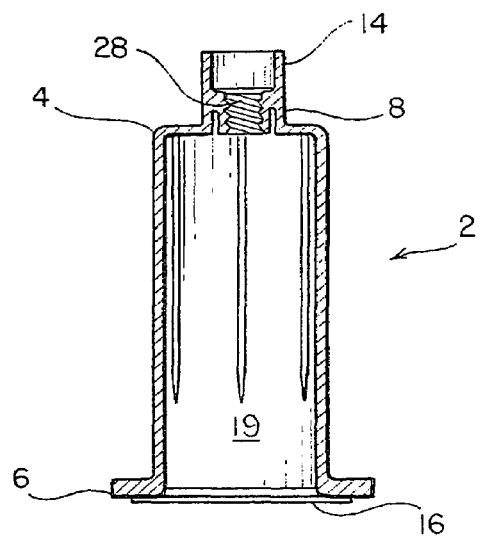
FIG. 4 is an improved holder of the instant invention.

As best shown in FIG. 4, holder 2 of the instant invention device has a sleeve 14 that extends, either integrally or otherwise, from neck 8. Moreover, enclosing the opening of the distal end 6 of holder 2 is a cover 16 that may be paper or other types of materials that would allow a sterilizing gas such as for example ethylene oxide (ETO) to pass into space 19 of the housing, and yet at the same time prevents bacteria or other contaminants from intruding or passing into space 19.

Figure 2:
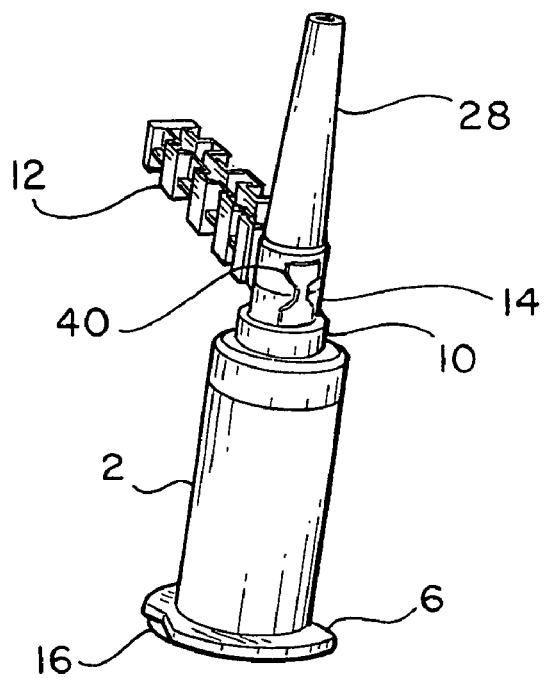
FIG. 2 is a perspective view of the safety device of the instant invention shown fully assembled.
Figure 5:
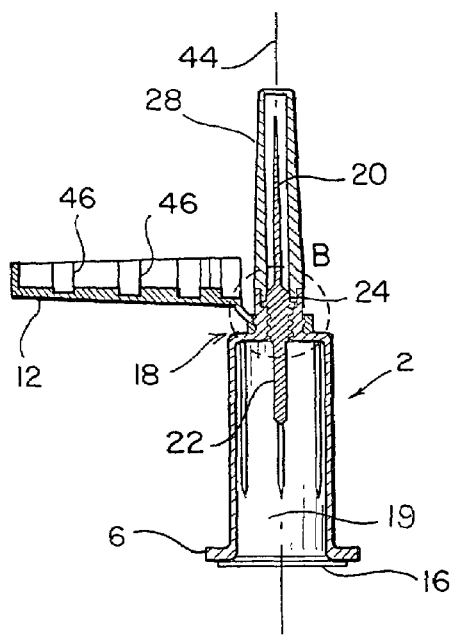
FIG. 5 is a cross-sectional view of the device of the instant invention.

With reference to FIGS. 2 and 5, the device of the instant invention is shown to include a double-ended needle assembly 18 fitted to neck 8 of holder 2. Double-ended needle assembly 18 has a first cannula 20 that extends away from holder 2 and another cannula extending into space 19 of holder 2, and which is shown to be covered by a rubber shroud 22. Needle assembly 18 has a base, or hub, 24 that includes a threaded portion 26 that is threaded to the internal threads 29 of neck 8. Once fully threaded into neck 8, base 24 is substantially positioned within sleeve 14. Although shown as being threadedly mated, in practice, for the instant invention, hub 24 of needle assembly 18 may be press fitted to neck 8. Hub 24 may be threaded to neck 8 of holder 2 with a torque force sufficient to ensure that once fitted, hub 24 could not be removed from neck 8.

Enveloping cannula 20 is a sheath or cap 28. As best shown in the cross-sectional view of FIG. 6, sheath 28 is fitted to sleeve 14 in a relatively secured and tight manner. Given the respective configurations of sleeve 14, base 24 and sheath 28, and their interrelationship, a tortuous path 30 is established between the interacting surfaces 28s, 14s and 24s of sheath 28, sleeve 14 and base 24, respectively. With the aid of appropriate vents 32 etched to hub 24, tortuous path 30 allows gasses such as the ETO gas to seep into space 34 enclosed by sheath 28 to sterilize needle 20 and the surfaces enclosed by sheath 28 within space 34, while at the same time creates a seal or barrier against bacteria and other contaminants from entering into space 34.

Another route via which sterilizing gas may be routed to space 34 is by way of space 19 of holder 2. The path of the sterilizing gas from holder 2 is indicated by directional arrow 36. The threads 26t of the threaded portion 26 of hub 24 are configured such that, when mated with the internal threads 29 of neck 8, spaces such as 38 are effected between threaded portion 26 and neck 8. Thus, sterilizing gas could in fact be routed to space 34 by way of the opening at holder 2. As was noted earlier, cover 16 heat sealed to distal end 6 of holder 2 prevents bacteria from intruding into space 19 of holder 2 while at the same time allows sterilizing gas to enter into space 19 and, from there, eventually into space 34 defined by sheath 28. Cannula 20 may therefore be sterilized by the ETO gas input into space 34 either by way of tortuous path 30 or by way of arrow 36. It should be noted, however, given that tortuous path 30 is closer to space 34, most of the sterilization of space 34 in fact would be effected by way of tortuous path 30.

Since the device of the present invention is self contained and appropriately sealed, multiple devices of the present invention may be conveyed to a sterilization room en masse so as to be readily sterilized.

To ensure that the sterility of the device of the instant invention is not tampered with, a tamper evident seal 40, which may be made of paper, is fixed to both the lower portion of sheath 28 and sleeve 14. Any breakage of seal 40 indicates that the device may have been tampered with and that the sterility of the device is open to question. In the same vein, given that cover 16 is heat sealed to the base of distal end 6 of holder 2, once removed, cover 16 could no longer be reattached to the base of holder 2. Thus, any partial removal of cover 16 from distal end 6 of holder 2 is an indication that holder 2 may no longer be sterile.

Given that the device, as best shown in FIG. 2, is all pre-assembled and sterilized, the convenience with which the device of FIG. 2 may be used to withdraw blood from a patient is, without question, greater than that disclosed in the aforenoted incorporated by reference patents. So, too, the fact that the device is a sterile use once only device ensures that no cross-contamination could take place.

Figure 6:
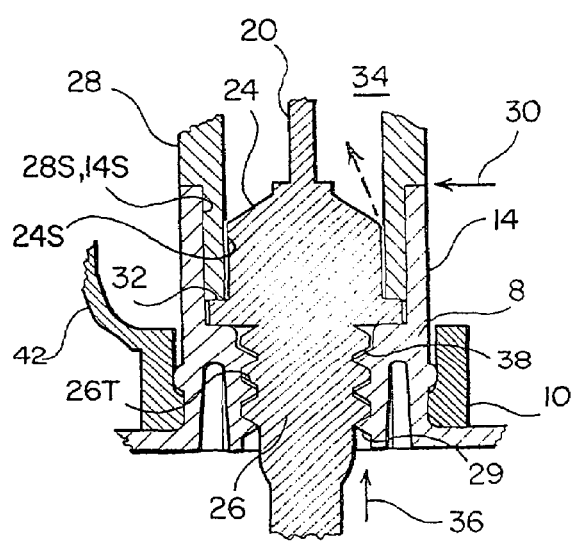
FIG. 6 is an enlarged view of the circled area of the FIG. 5 drawing.

The device of the instant invention, as best shown in FIGS. 2, 5 and 6, has fitted about its neck 8 a collar 10, which in turn has attached thereto, by means of a hinge 42, a housing 12 that is pivotable from the position as shown in FIG. 5 to a position substantially along the length of the longitudinal axis 44 of the device. A number of mechanisms in the form of hooks 46 may be integrally provided in housing 12. alternatively, corresponding locking mechanisms such as for example anchors and clasping fingers may be provided at the lower portion of housing 12 and either sleeve 14 or collar 10 so that once housing 12 is pivoted to the position as indicated by longitudinal axis 14, those coacting mechanisms would coact to fixedly retain housing 12 in the longitudinal direction, thereby enveloping needle or cannula 20. Of course, this is done after sheath 28 has been removed. The particulars of the coacting locking mechanisms at the housing 12 and collar 10 are disclosed in U.S. Pat. No. 5,469,622, the disclosure of which is incorporated by reference herein.

In the case where only the integral hooks 46 are present in housing 12, after sheath 28 is removed from sleeve 14, to cap cannula 20, assuming that it has been used and therefore has been contaminated, a user only needs to pivot housing 12 to the direction of longitudinal axis 44 so as to have hooks 14 first bias against cannula 20 and then fixedly grasping cannula 20 after housing 12 is moved to its final position, as the hooks flex back to their respective original positions. It should be appreciated that both the hooks integrated to the inside of housing 12 and the coacting locking mechanisms at housing 12 and collar 10, or sleeve 14, could be configured in the device of the instant invention.

A second embodiment of the instant invention is shown in FIGS. 7 and 8. For this embodiment, sleeve 14, instead of being an integral extension of neck 8, is a separate piece in the shape of a cup, with its bottom portion having an opening 48 that matches the opening of neck 8. For this embodiment, sleeve 14 acts as a sealing gasket, once end 22 of the double-ended needle assembly 18 is passed through opening 48 of sleeve 14 and hub 24 threadedly mated to neck 8. Sleeve 14 is held in place by the action of bottom surface 24b of hub 24 of the needle assembly against the bottom surface of sleeve 14. Thus, once assembled as shown in FIG. 8, the same tortuous path such as 30 shown in FIG. 6 is likewise established for the embodiment of the invention as shown in FIGS. 7 and 8.

Inasmuch as the present invention is subject to many variations, modifications and changes in detail, it is intended that all matter described throughout this specification and shown in the accompanying drawings be interpreted as illustrative only and not in a limiting sense. For example, instead of a blood drawing device, the instant invention may also encompass a syringe device that has fitted thereto the as shown needle protection housing 12. To maintain sterility of the needle, which is capped by a sheath, a sleeve such as 14 may also be fitted to such syringe so as to establish a tortuous path whereby the space defined by the sheath may be sterilized at the factory. It should therefore be appreciated that instead of a double-ended needle assembly, devices that uses a cannula that has a hub that fits to an end of a body, for example a luer end, may also be prepackaged as a single sterilized unit. Accordingly, it is intended that the invention be limited only by the spirit and scope of the hereto appended claims.

The invention claimed is:

1. Apparatus, comprising:
   a holder having one and other ends, said one end having an extension and a sleeve extending from said extension;
   a double ended needle having a base mated to said extension of said one end of said holder, one end of said needle extends away from said holder while other end of said needle extends into said holder, said base of said needle being substantially positioned within said sleeve;
   a collar mounted about said extension;
   a housing pivotally extending from said collar;
   a sheath having an open end, said open end having a circumference that enables the sheath to matingly fit to said sleeve to establish an environment sealed against bacteria intrusion for said one end of said needle.

2. Apparatus of claim 1, wherein the surface of the open end of said sheath and the surface of said sleeve that come into contact with each other effect at least one portion of a tortuous path to act as a barrier to seal the inside of said sheath against potential bacteria intrusion.

3. Apparatus of claim 1, wherein said sleeve integrally extends from said extension.

4. Apparatus of claim 1, wherein said sleeve comprises a semi-closed end having an opening substantially matching the opening of said extension and through which the portion of said base of said needle that mates to said extension passes, said sleeve sealingly fitting onto said extension when said base of said needle is mated to said extension.

5. Apparatus of claim 1, wherein said housing further comprises an integral locking means for grasping said one end of said needle when said housing is pivoted to cover said one end of said needle after said sheath has been removed from said sleeve.

6. Apparatus of claim 1, wherein said housing comprises at least one locking portion that coacts with at least another locking portion at said collar or said sleeve to fixedly retain said housing along a longitudinal axis of said holder to cover said one end of said needle after said sheath has been removed from said sleeve.

7. Apparatus of claim 1, further comprising:
   a cover sealing said other end of said holder to provide a sterile environment for the inside of said holder.

8. Apparatus of claim 1, wherein said collar is rotatable about said extension so that said housing is rotatable relative to said one end of said needle.

9. Apparatus of claim 1, further comprising:
   means on said sheath and said sleeve to provide evidence that the sealed environment of said one end of said needle has been compromised.

10. Blood drawing device comprising a holder having one and other ends, said one end having a neck to which a sleeve extends, a double ended needle connected to said neck via a base so that one end of said needle extends away from said holder and other end of said needle extends within said holder, a collar having a housing pivotally connected thereto mounted about said neck, a sheath having an open end matingly fitted to said sleeve, wherein said base is positioned substantially within said sleeve and said open end of said sheath is fitted to said sleeve in such a way that said sleeve, said base and said open end of said sheath in combination establish an environment impervious to bacteria intrusion for the space inside said sheath that encloses said one end of said needle.

11. Device of claim 10, wherein the surfaces of said sheath that come into contact with the respective surfaces of said base and said sleeve effect a tortuous path act as a barrier to prevent contaminants from entering said space inside said sheath that encloses said one end of said needle.

12. Device of claim 10, wherein said sleeve integrally extends from said neck.

13. Device of claim 10, wherein said sleeve comprises a semi-closed end having an opening substantially matching the opening of said neck sealingly fitted onto said neck when said needle is connected to said neck.

14. Device of claim 10, wherein said housing further comprises an integral locking means for grasping said needle when said housing is pivoted to cover said needle after said sheath has been removed from said sleeve.

15. Device of claim 10, wherein said housing comprises at least one locking portion that coacts with at least an other locking portion at said collar or said sleeve to fixedly retain said housing along a longitudinal axis of said holder to cover said needle after said sheath has been removed from said sleeve.

16. Device of claim 10, further comprising:
   a cover sealing said other end of said holder to provide a sterile environment for the inside of said holder; and
   a tamper seal on said sheath and sleeve that, when broken, provides evidence that the sealed environment of said needle has been compromised.

17. Device of claim 10, wherein said collar is rotatable about said neck and said housing is rotatable relative to said needle.

18. A needle device comprising a body having a neck to which a needle is connected via a base, a sleeve extending from said neck to enclose said base, a collar having a housing for covering said needle pivotally connected thereto mounted about said neck, a sheath having an open end matingly fitted to said sleeve, said sleeve, said base and said open end of said sheath that mates to said sleeve in combination establish an environment for the space inside said sheath that encloses said needle that is impervious to bacteria or contaminant intrusion.

19. Device of claim 18, wherein the surfaces of said sheath that come into contact with the respective surfaces of said base and said sleeve effect a tortuous path to act as a barrier to prevent bacteria or other contaminants from entering said space inside said sheath that encloses said one end of said needle.

20. Device of claim 18, wherein said sleeve integrally extends from said neck.

21. Device of claim 18, whereIn said sleeve comprises a semi-closed end having an opening substantially matching the opening of said neck sealingly fitted onto said neck when said needle is connected to said neck.

22. Device of claim 18, wherein said housing further comprises an integral locking means for grasping said needle when said housing is pivoted to cover said needle after said sheath has been removed from said sleeve.

23. Device of claim 18, wherein said housing comprises at least one locking portion that coacts with at least an other locking portion at said collar or said sleeve to fixedly retain said housing along a longitudinal axis of said holder to cover said needle after said sheath has been removed from said sleeve.

24. Device of claim 18, further comprising:
a tamper evident seal on said sheath and sleeve that, when broken, provides evidence that the sealed environment of said needle has been compromised.

25. Device of claim 18, wherein said collar is rotatable about said neck and said housing is rotatable relative to said needle.

26. Device of claim 18, wherein said body comprises a Vacutainer holder having one end wherefrom said neck extends and an other open end sealed with a cover to provide a sterile environment within said holder.

* * * * *